(12) United States Patent
Deshaies et al.

(10) Patent No.: US 6,413,725 B1
(45) Date of Patent: *Jul. 2, 2002

(54) BIOCHEMICAL ASSAY TO MONITOR THE UBIQUITIN LIGASE ACTIVITIES OF CULLINS

(75) Inventors: Raymond J. Deshaies, Claremont; R. M. Renny Feldman, San Marino, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/370,011

(22) Filed: Aug. 6, 1999

Related U.S. Application Data

(60) Provisional application No. 60/095,831, filed on Aug. 7, 1998.

(51) Int. Cl.[7] .................. G01N 33/53; G01N 33/573

(52) U.S. Cl. .................. 435/7.1; 435/4; 435/6; 435/7; 435/7.21; 435/23; 435/29; 435/69.1; 435/193; 435/7.2; 435/440; 435/455; 435/325; 435/410; 435/243; 435/254.2; 435/320.1; 435/183; 435/5; 436/95; 436/120; 436/119; 436/169; 436/170; 436/500; 436/806; 436/808; 536/23.1; 536/23.2; 536/23.5; 536/24.3; 536/24.31; 536/24.33; 530/387.9; 530/300; 530/350

(58) Field of Search .............. 435/4, 6, 7, 7.1, 435/7.21, 23, 29, 69.1, 193, 7.2, 455, 440, 325, 410, 243, 254.2, 320.1, 183, 15; 436/806, 500, 95, 119, 120, 808, 169, 170; 530/350, 300, 387.9; 536/23.1, 23.2, 23.5, 24.3, 24.31, 24.33

(56) References Cited

U.S. PATENT DOCUMENTS

| | | | | |
|---|---|---|---|---|
| 5,976,849 A | * | 11/1999 | Hustad et al. .......... 435/183 |
| 6,060,262 A | * | 5/2000 | Beer-Romero et al. ...... 435/15 |
| 6,068,982 A | * | 5/2000 | Rolfe et al. .......... 435/7.21 |
| 6,165,731 A | * | 12/2000 | Deshaies et al. ......... 435/7.1 |
| 6,180,379 B1 | * | 1/2001 | Ruderman et al. ........ 435/193 |

OTHER PUBLICATIONS

Sommer et al., Experientia, 48, 1992, pp. 172–178.*
Feldman et al., Cell, vol. 91, 1997, pp. 221–230.*
Feldman et al., "A Complex of Cdc4p, Skp1p, and Cdc53p/Cullin Catalyzes Ubiquitination of the Phosphorylated CDK Inhibitor Sic1p," Cell 91:221–230 (Oct. 17, 1997).
Lyapina et al., "Human CUL1 forms an evolutionarily conserved ubiquitin ligase complex (SCF) with SKP1 and an F–box protein," Proc. Natl. Acad. Sci. USA 95:7451–7456 (Jun. 1998).

* cited by examiner

Primary Examiner—Christopher L. Chin
Assistant Examiner—Lisa V Cook
(74) Attorney, Agent, or Firm—Gray Cary Ware & Friedenrich LLP; Lisa A. Haile

(57) ABSTRACT

The present invention is based on the discovery of a simplified assay for identifying modulators of ubiquitin ligase activity. This assay allows detection of compounds that affect ubiquitination and thus, cell cycle regulation in cells. An increase in ubiquitination, in comparison to a test sample lacking a test compound, indicates a stimulation of activity, whereas a reduction in ubiquitination indicates an inhibitor of activity. Also disclosed herein are methods of identifying proteins having ubiquitin ligase activity, methods of identifying substrates for ubiquitination, methods for identifying an activity relationship between a particular ubiquitin ligase and a particular ubiquitin conjugating enzyme, and chimeric proteins comprising a ubiquitin conjugating enzyme and a ubiquitination substrate, which are useful in all of the disclosed methods.

15 Claims, 1 Drawing Sheet

A general scheme for assaying the ubiquitin ligase activity of cullins

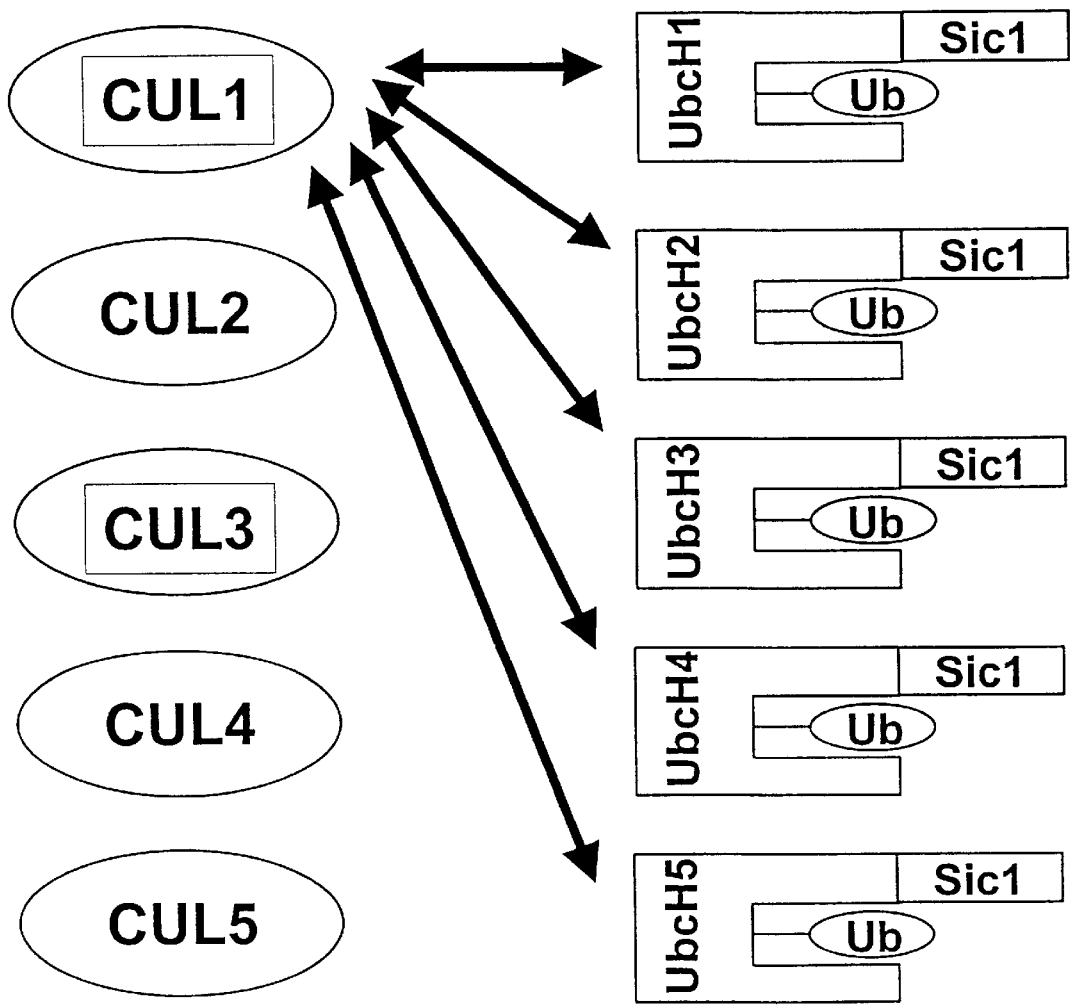

BIOCHEMICAL ASSAY TO MONITOR THE UBIQUITIN LIGASE ACTIVITIES OF CULLINS

CROSS REFERENCE TO RELATED APPLICATIONS

This application claims priority under 35 U.S.C. 119(e)(1) to U.S. Provisional Application No. 60/095,831, filed on Aug. 7, 1998, which is incorporated herein by reference.

STATEMENT AS TO FEDERALLY SPONSORED RESEARCH

This invention was made with Government support under Grant No. GM 52466-01 awarded by the National Institutes of Health. The Government has certain rights in this invention.

FIELD OF THE INVENTION

This invention relates generally to the field of cell cycle control and more specifically to the role of ubiquitination in the regulation of cell cycle progression.

BACKGROUND OF THE INVENTION

The irreversible nature of proteolysis makes it well-suited to serve as a regulatory switch for controlling unidirectional processes. This principle is evident in the control of the cell cycle, where initiation of DNA replication, chromosome segregation, and exit from mitosis are triggered by the destruction of key regulatory proteins (Schwob et al., *Cell* 79:233–244, 1994; Glotzer et al., *Nature* 349:132–138, 1991; Cohen-Fix, et al., *Genes Dev.* 10:3081–3093, 1996). Proteins are typically marked for proteolytic degradation by attachment of multiubiquitin chains.

In the early 1970s a novel protein was extracted from bovine thymus which was thought to have properties relating to the differentiation of T and B lymphocytes. This same protein was later found to be not only in the thymus but in all other eukaryotic cells. Due to its ubiquitous nature, the new protein was named ubiquitous immunopoietic polypeptide (Goldstein et al., *Proc. Natl. Acad. Sci. U.S.A.* 72: 11–15, 1975). Another protein of similar molecular weight was also discovered, and seemed to be involved in the ATP dependant degradation of denatured globulin in reticulocytes (Ciechanover et al., *Biochem. Biophys. Res. Commun.* 81,1100–1105, 1978).

This protein was a small protein made up of only 76 amino acids, and is now known as ubiquitin. Ubiquitin has many diverse functions, and is one of the most highly conserved sequences of all proteins found in eukaryotic cells, with only minor variations of two or three amino acids found between organisms as evolutionarily dissimilar as mammals, oats, and yeasts (Özkaynak et al., *EMBO J.* 6(5):1429–1439, 1987).

Ubiquitin may have many roles in cell function including the mediation of various stress responses, repair of damaged DNA, regulation of differential gene expression, modification of histones and receptors, effects in neurodegenerative diseases, and control of the cell cycle. Other novel functions also suggested include the behavior of ubiquitin in a 'chaperone-like' role in the assembly of ribosomal proteins and as a response to heat shock. However, the most important role appears to be the role ubiquitin plays in selective protein degradation. The ability of ubiquitin to target proteins for degradation gives it a key role in the regulation of the cell cycle.

Many of the enzymes involved in ubiquitin dependant proteolysis have been identified, and the mechanism by which certain proteins are degraded has been determined. The presence of at least two different components required for ubiquitin dependant proteolysis have been confirmed, and that the mechanism of degradation is known to require the utilization of energy obtained from ATP (Ciechanover et al., *Proc. Natl. Acad. Sci. U.S.A.* 77:1365–1368, 1980).

The first step in selective degradation is the ligation of one or more ubiquitin molecules to a protein substrate (Hershko et al., *Proc. Natl. Acad. Sci. U.S.A.* 77:1783–1786, 1980). This process is initiated by ubiquitin-activating enzyme (E1), which activates ubiquitin by adenylation and becomes linked to it via a thiolester bond. Ubiquitin is then transferred to a ubiquitin-conjugating enzyme, E2. Whereas E2s can directly attach ubiquitin to lysine residues in a substrate, most physiological ubiquitination reactions probably require a ubiquitin ligase, or E3 (Hershko et al., *J. Biol. Chem.* 258:8206–8214, 1983). E3s have been implicated in substrate recognition and, in one case, transfer of ubiquitin from E2 to a substrate via an E3~ubiquitin-thiolester intermediate (Scheffner et al., *Nature* 373:81–83, 1995). Once the substrate is multiubiquitinated, it is then recognized and degraded by the 26S proteasome.

A novel ubiquitination pathway has recently been discovered in budding yeast. Components of this pathway include the Cdc53, Cdc4, and Skp1 gene products, which assemble into a ubiquitin ligase complex known as $SCF^{Cdc4}$ (for Skp1, Cullin, F-box protein Cdc4). In yeast, SCF collaborates with the E2 enzyme Cdc34 to catalyze ubiquitination of the CDK inhibitor Sic1. The specificity of SCF is thought to be governed by Skp1 and the F-box-containing subunit Cdc4, which together form a substrate receptor that tethers Sic1 to the complex. The assembly of this receptor is thought to be mediated by a direct interaction between yeast Skp1 and the F-box domain of Cdc4 (Feldman et al., *Cell* 21:221–230, 1997; Skowyra et al., *Cell* 91:209–219, 1997)

Whereas genetic analysis has revealed that Sic1 proteolysis requires Cdc4, G1 cyclin proteolysis depends upon a distinct F-box-containing protein known as GRR1 (Barral et al., *Genes Dev.* 9:399–409, 1995). Alternative SCF complexes ($SCF^{GRR1}$) assembled with GRR1 instead of Cdc4 bind G1 cyclins but not Sic1, suggesting that there exist multiple SCF complexes in yeast whose substrate specificities are dictated by the identity of the F-box subunit.

Components of the SCF ubiquitination pathway have been highly conserved during evolution. Human homologues of the yeast Cdc34 and Skp1 have been reported (Plon et al., *Proc. Natl. Acad Sci. USA* 90:10484–10488, 1993; Zhang et al., *Cell* 82:912–925, 1995), and F-box-containing proteins like Cdc4 and GRR1 have been identified in many eukaryotes (Bai et al., *Cell* 86:263–274, 1996). Many of these F-box proteins also contain either WD-40 repeats (like Cdc4) or leucine-rich repeats (like GRR1). A potential human counterpart of GRR1, SKP2, has been identified along with human Skp1 as a Cyclin A/CDK2-associated protein that is necessary for S-phase progression (Zhang et al., *Cell* 82:912–925, 1995). Homologues of Cdc53, which are known as Cullins, are also present in many eukaryotes, including humans and nematodes (Kipreos et al., *Cell* 85:1–20, 1996; Mathias et al., *Mol. Cell. Biol.* 16:6634–6643, 1996).

It is currently thought that transitions from one phase of the cell cycle to another are coupled to fluctuations in the activity of a family of cyclin-dependent protein kinases (CDKs). These kinases represent a special family of kinases that are activated by regulatory proteins known as cyclins. Cyclins bind to the catalytic kinase subunit and trigger a battery of post-translational modifications that culminate in the activation of the kinase. Eventually, the kinase activity is extinguished by proteolysis of the stimulatory cyclin subunit. In yeast, a crucial means of regulating cell cycle progression is by the targeted degradation of both activating and inhibitory subunits of the cyclin dependent kinase Cdc28. The G1 to S phase transition is driven by the destruction of an inhibitor (Sic1) that restrains the activity of a cyclin/CDK complex that triggers DNA replication. The ubiquitin conjugating enzyme Cdc34 has been implicated in the ubiquitination of the regulatory proteins and their ultimate destruction (Goebl et al., *Science* 241:1331–5, 1988).

The two other proteins in the SCF complex, Cdc4 and Cdc53, have been found to be required for the G1 to S phase transition. The absence of functional Cdc4, Cdc34 or Cdc53 from the cell gives rise to identical terminal morphologies suggesting that these proteins interact to perform a function. Numerous genetic interactions are seen between these genes and the encoded proteins are found physically associated in vivo. Thus, the G1 to S phase transition in the yeast cell cycle requires the activity of a complex containing Cdc4, Cdc34 and Cdc53. Identification of counterparts of Cdc4, Cdc34, and Cdc53 in other species such as humans will provide new insights into how disturbances in ubiquitination influence diseases associated with cell proliferation.

Several human cell cycle regulators are targeted for ubiquitination following their phosphorylation by CDKs, implicating them as potential substrates of SCF pathway(s) in human cells. Among them is the CDK inhibitor p27, the abundance of which may be regulated by Cdc34-dependent ubiquitination (Pagano et al., *Science* 269:682–685, 1995; Sheaff, R. J., et al., *Genes Dev.* 11:1464–1478, 1997). In addition, Cyclins E and D1 are degraded by a ubiquitin-dependent pathway following phosphorylation at a specific site (e.g., Won & Reed, *EMBO J.* 15:4182–4193, 1996). It has also been suggested that cyclin A is a target of an SCF pathway. Alternatively, SCF-bound Cyclin A/CDK2 may phosphorylate SCF subunits or potential substrates such as E2F-1/DP-1, thereby activating SCF-dependent ubiquitination (Dynlacht et al., *Genes Dev.* 8:1772–1786, 1994).

Ubiquitination is also thought to play a role in tumor formation, as the ubiquitin system is associated with cell cycle regulation (King, R. W., et al., *Science*, 274:1652–9, 1996). For example, the protein E6, encoded by the human papilloma virus, which causes cervical cancer, was found to bind to a human ubiquitin-protein ligase, thereby targeting the tumor suppressor p53 for ubiquitin-mediated degradation (Scheffner et al., *Cell* 63:1129–36, 1990; Huibregtse et al., *Molecular and Cellular Biology* 13:775–84, 1993). A need exists, therefore, for assay systems that can identify modulators of ubiquitin ligase activity, some of which may be useful as therapeutic treatments. The present invention addresses this need.

SUMMARY OF THE INVENTION

The present invention is based on the discovery of a simplified assay for identifying modulators of ubiquitin ligase activity. This assay allows detection of compounds that affect ubiquitination and thus, cell cycle regulation in cells. Thus, the invention provides a method and assay system for identifying modulators of ubiquitin ligase activity comprising contacting a test sample composed of a ubiquitin ligase, an E1 enzyme, ubiquitin, ATP, and a substrate with a test compound under suitable test conditions and measuring the ubiquitination of the substrate. An increase in ubiquitination, in comparison to a test sample lacking a test compound, indicates a stimulation of activity, whereas a reduction in ubiquitination indicates an inhibitor of activity.

Also disclosed herein are methods of identifying proteins having ubiquitin ligase activity, methods of identifying substrates for ubiquitination, methods for identifying an activity relationship between a particular ubiquitin ligase and a particular ubiquitin conjugating enzyme, and chimeric proteins comprising a ubiquitin conjugating enzyme and a ubiquitination substrate, which are useful in all of the disclosed methods.

SUMMARY OF THE FIGURES

FIG. 1 shows a schematic representation of a general scheme for evaluating ubiquitin ligase activity using ubiquiting conjugating enzyme:substrate chimeric proteins. A ubiquitin ligase is incubated with a particular chimera in the presence of an E1 enzyme, ubiquitin,. and ATP. Autoubiquitination of the chimera is measured to determine the activity relationship between the ubiquitin ligase and the ubiquitin conjugating enzyme.

DESCRIPTION OF THE PREFERRED EMBODIMENTS

The present invention relates to the role of ubiquitination and a biochemical assay to monitor the activities of ubiquitin ligases. These methods and assays are useful in the detection of agents that modulate the activities of these polypeptides in ubiquitination, and the in the identification of novel components of the ubiquitin pathway. The invention is based, in part, on the discovery that although ubiquitin ligases exist as one component in a multi-component complex when present in their native cellular environment, their activity is detectable in a simple assay system composed of isolated proteins. Thus, screening assays can be created without requiring a detailed knowledge of the identities of all of the physiological elements of a ubiquitination pathway.

It must be noted that as used herein and in the appended claims, the singular forms "a," "and," and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

Unless defined otherwise, all technical and scientific terms used herein have the same meaning as commonly understood to one of ordinary skill in the art to which this invention belongs. Although any polypeptides, compounds and materials similar or equivalent to those described herein can be used in the practice or testing of the invention, the preferred methods, devices and materials are now described.

All publications mentioned herein are incorporated herein by reference in full for the purpose of describing and disclosing the cell lines, antibodies, and methodologies which are described in the publications which might be used in connection with the presently described invention. The publications discussed above and throughout the text are provided for their disclosure prior to the filing date of the present application.

In one embodiment, the invention provides a method of identifying compounds that modulate an activity of a ubiquitin ligase comprising: contacting a test sample with a test compound under suitable test conditions, wherein the test sample comprises an ubiquitin ligase, an E1 enzyme, ubiquitin, adenosine 5'triphosphate (ATP), a ubiquitin conjugating enzyme and a substrate; measuring the ubiquitination of the substrate; and comparing the level of ubiquitination of the substrate in the test sample with the ubiquitination of a substrate incubated under the same test conditions in the absence of test compound. The level of ubiquitination of the substrate in the test sample is indicative of the ability of the test compound to modulate ubiquitin ligase activity. An increase in the level of ubiquitination is an indication that ubiquitin ligase activity has been stimulated, whereas a decrease in the level of ubiquitination is an indication that ubiquitin ligase activity has been inhibited.

E1 enzyme is well known to one of skill in the art (e.g., Hershko et al., *Ann. Rev. Biochem.* 61:761–807, 1992, and Monia et al., *Biotechnol.* 8: 209–215, 1990, herein incorporated by reference). E1 enzyme initiates the ubiquitination process by activating ubiquitin. Any of the E1 enzymes known in the art are suitable for use in the invention method.

Ubiquitin ligases are key components in the ubiquitination of substrates. Suitable ubiquitin ligases that may be employed in the invention method include Cdc53, the Cdc53-related human cullins Cul1–Cul6, and the like. Cdc4, Cdc53, Skp1, and Cdc34 have been identified in *Saccharomyces cervisiae* as being essential for cell cycle progression. In yeast, Cdc4, Cdc34, Cdc53, and Skp1 have been cloned and mapped. "Yeast" includes members of the species *Saccharomyces cerevisiae* or any other yeast species. "Cdc53" is a polypeptide that acts with Cdc4 and Cdc34 to control the G1-S phase transition. Cdc53 activates the hydrolysis of an E2-ubiquitin thioester-bond linked complex and enables the ubiquitination of a substrate. Thus, Cdc53 assists in mediating the proteolysis of the CDK inhibitor Sic1 in late G1 (Mathias, N., et al., *Mol. Cell Biol.* 16:6634–6643). The "Cul polypeptides" are human polypeptides related to Cdc53 that can activate the hydrolysis of an E2-ubiquitin and enable the ubiquitination of a substrate (Kipreos et al., Cell 85:1–20, 1996, herein incorporated by reference). The Cul genes encode the polypeptides Cul1, Cul2, Cul3, Cul4a, Cul4b, and Cul5 and Cul6. As demonstrated herein, a Cul polypeptide (Cul1 p, see Examples below) can form an SCF complex with the yeast proteins Cdc4 and Skp1.

One preferred substrate is a ubiquitination conjugating enzyme. Ubiquitin conjugating enzymes transfer ubiquitin to lysine residues of suitable substrates. They also undergo autoubiquitinaiton, which can be measured by the assay methods disclosed herein. Suitable ubiquitin conjugating enzymes that can be employed in the invention method include Cdc34, UbcH1, UbcH2, UbcH3, UbcH4, UbcH5, UbcH6, UbcH7, UbcH10, L-UBC, and the like (see Kaiser, et al, FEBS Letts *350:1–4, 1994;* Kaiser, et al, FEBS Letts 377:193–196, 1995; Nuber, et al, J Biol Chem 271:2795–2800, 1996; Jensen, et al, J Biol Chem 270:30408–30414, 1995; Robinson, et al, Mamm Genome 6:725–731, 1995; and Plon et al., Proc. Natl. Acad. Sci. USA 90:10484–10488, all of which are herein incorporated by reference). "Cdc34" refers to a ubiquitin-conjugating enzyme isolated from yeast.

A second preferred substrate comprises a chimeric protein comprising a ubiquitin conjugating enzyme and a conjugation substrate. "Conjugation" or "ubiquitination" refers to the attachment of ubiquitin to a polypeptide by ubiquitin ligase/ubiquitin conjugating enzyme. A "conjugation substrate" is a polypeptide whose ubiquitination is promoted by ubiquitin ligase/ubiquitin conjugating enzyme. An example of a substrate is Sic1. "Sic1" refers to a polypeptide encoded by the Sic1 gene, which has been cloned and sequenced. In yeast, Sic1 is involved in the release from glucose repression, invertase expression, and sporulation (Celenza, et al., Mol. Cell Biol. 9:5045–5054; Nugroho et al. *Mol. Cell Biol.* 3320–8, 1994). Ubiquitinated Sic1 is then targeted for degradation by a ubiquitin dependent protease as part of promoting DNA replication. Other suitable substrates include p53, cyclin D1, cyclin E, cyclin A/CDK2, G1 cyclin, and the like.

As used in connection with the present invention the term "polypeptide" refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" as used herein is intended to encompass any amino acid sequence and include modified sequences such as glycoproteins. The term polypeptide is specifically intended to cover naturally occurring proteins, as well as those which are recombinantly or synthetically synthesized. Fragments are a portion of a protein. Fragments can have the same or substantially the same amino acid sequence as the naturally occurring protein. Substantially the same means that an amino acid sequence is largely, but not entirely, the same, but retains a functional activity of the sequence to which it is related, for example, the fragment may bind to an antibody that also recognizes the full length polypeptide. In general two amino acid sequences are substantially the same or substantially homologous if they are at least 85% identical.

The term "substantially purified" as used herein refers to a polypeptide which is substantially free of other proteins, lipids, carbohydrates or other materials with which it is naturally associated. In one embodiment the substantially purified polypeptide comprises at least 80% dry weight, preferably 95–99% dry weight of a polypeptide of interest. One skilled in the art can purify polypeptides, such as Culs 1–6, using standard techniques for protein purification. The substantially pure polypeptide will yield a single major band on a non-reducing polyacrylamide gel. The purity of the polypeptide can also be determined by amino-terminal amino acid sequence analysis.

As used herein, the term "functional polypeptide" refers to a polypeptide which possesses biological function or activity which is identified through a defined functional assay and which is associated with a particular biologic, morphologic, or phenotypic alteration in the cell. The term functional fragments of a polypeptide, refers to all fragments of a polypeptide that retain an activity of the polypeptide. In one specific, nonlimiting example a functional fragment of Cdc53 retains the ability to function as part of an SCF complex and thereby ubiquitinate Sic1. Biologically functional fragments, for example, can vary in size from a polypeptide fragment as small as an epitope capable of binding an antibody molecule to a large polypeptide capable of participating in the characteristic induction or programming of phenotypic changes within a cell.

Minor modifications of the primary amino acid sequences of a polypeptide may result in a polypeptide which has substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the polypeptide still exists. Further, deletion of one or more amino acids can also result in a modification of the structure of the resultant molecule without significantly altering its activity. Deletion can lead to the development of a smaller active molecule which could have broader utility. For example, it may be possible to remove amino or carboxy terminal amino acids and retain an activity of a ubiquitin ligase.

The polypeptides of the invention include conservative variations of the native polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

A compound can modulate the activity of a ubiquitin ligase by either stimulating or inhibiting the ubiquitination of the substrate. A compound inhibits ubiquitination if the level of the substrate that is ubiquitinated is decreased as compared with the level of substrate ubiquitinated in the absence of the test compound. In one embodiment, the compound inhibits ubiquitination by 50% or more as compared to a control sample not contacted with the compound. A compound stimulates ubiquitination if the fraction of the substrate that is ubiquitinated or the amount of ubiquitin incorporated into substrate is increased as compared to reactions performed in the absence of the test compound. In one embodiment, the compound stimulates ubiquitination by 50% or more as compared to a control sample not contacted with the compound.

The phrase "compound that modulates an activity of a ubiquitin ligase" denotes derivatives of antibodies, peptides, chemical compounds or pharmaceuticals that affect an activity of an ubiquitin ligase. The term "compound" or "test compound" includes both biologic agents and chemical compounds ("small molecules"). The determination and isolation of compounds is well described in the art. (See, e.g., Lerner, *Trends NeuroSci.* 17:142–146, 1994, which is hereby incorporated in its entirety by reference.) "Incubating" includes conditions which allow contact between the test compound and the other assay components. Contacting includes in solution and in solid phase.

The test compound may optionally be a combinatorial library for screening a plurality of compositions. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Any of a variety of procedures may be used to clone the genes of use with the method of the present invention when the test compound is in a combinatorial library or is expressed as a gene product (as opposed to a chemical compound). One such method entails analyzing a shuttle vector library of DNA inserts (derived from a cell which expresses the compound) for the presence of an insert which contains the composition gene. Such an analysis may be conducted by transfecting cells with the vector and then assaying for expression of the composition binding activity. The preferred method for cloning these genes entails determining the amino acid sequence of the composition protein. Usually this task will be accomplished by purifying the desired composition protein and analyzing it with automated sequencers. Alternatively, each protein may be fragmented as with cyanogen bromide, or with proteases such as papain, chymotrypsin or trypsin (Oike, Y., et al., *J. Biol. Chem.*, 257:9751–9758, 1982; Liu, C., et al., *Int. J. Pept. Protein Res.*, 21:209–215, 1983). Although it is possible to determine the entire amino acid sequence of these proteins, it is preferable to determine the sequence of peptide fragments of these molecules.

The compounds of the present invention can be extracted and purified from the culture media or a cell by using known protein purification techniques commonly employed, such as extraction, precipitation, ion exchange chromatography, affinity chromatography, gel filtration and the like. Compounds can be isolated by affinity chromatography using the modified receptor protein extracellular domain bound to a column matrix or by heparin chromatography.

In one embodiment the compound is an antibody, or a biologically active fragment thereof, which interferes with or binds to an ubiquitin ligase or an ubiquitin conjugating enzyme. Polypeptide components of the invention assay can be used to produce antibodies which are immunoreactive or bind to epitopes of the polypeptide of interest. Antibodies which consist essentially of pooled monoclonal antibodies with different epitopic specificities, as well as distinct monoclonal antibody preparations are included. The invention includes the use of commercially available monoclonal antibodies which recognize Cul1, Cdc53, or Cdc34.

Polyclonal antibodies can also be used in the method of the invention. The preparation of polyclonal antibodies is well-known to those skilled in the art. See, for example, Green et al., Production of Polyclonal Antisera, in: *Immunochemical Protocols*, pages 1–5, Manson, ed., Humana Press, 1992; Coligan et al., Production of Polyclonal Antisera in Rabbits, Rats, Mice and Hamsters, in: *Current Protocols in Immunology*, section 2.4.1, 1992, which are hereby incorporated by reference.

The preparation of additional monoclonal antibodies likewise is conventional. See, for example, Kohler & Milstein, *Nature* 256:495, 1975; Coligan et al., sections 2.5.1–2.6.7; and Harlow et al., in: *Antibodies: a Laboratory Manual*, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., Purification of Immunoglobulin G (IgG), in: *Methods in Molecular Biology*, Vol. 10, pages 79–104, Humana Press, 1992.

Alternatively, an antibody that binds an ubiquitin ligase or ubiquitin conjugating enzyme may be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989, which is hereby incorporated in its entirety by reference. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993, which are hereby incorporated by reference.

Antibodies of the invention also may be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994, which are hereby incorporated by reference. Cloning and expression vectors that are useful for producing a human immunoglobulin phage library can be obtained, for example, from STRATAGENE Cloning Systems (La Jolla, Calif.).

The term antibody as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York, 1988, incorporated herein by reference). As used in this invention, the term epitope means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The effect of the compound on the activity of a polypeptide subunit of an ubiquitin ligase is measured by measuring the ubiquitination of a substrate. Assays for ubiquitination are well known to one of skill in the art. In one embodiment, the ubiquitin used in the method of the invention is a derivatized ubiquitin. A "derivatized ubiquitin" is a ubiquitin molecule including a label that is readily identified. For example, the derivatized ubiquitin can be an $^{125}$I-ubiquitin, a fluorescent ubiquitin, a glutathione S-transferase conjugated ubiquitin and a biotinylated ubiquitin. Using assays well known in the art, the presence of the label, and thus the amount of derivatized ubiquitination, can be identified.

Ubiquitination results in an increase in the molecular weight of the substrate. Thus any assay which measures molecular weight of the substrate, such as SDS-poly acrylamide gel electrophoresis, can be used to measure ubiquitination. This assay can be readily adapted to the large scale screening of compound libraries by converting it to a solid phase format. In one specific nonlimiting example, ubiquitination assays can be performed with an appropriately engineered substrate in microtiter plate in the presence of a derivatized ubiquitin. For example, the ubiquitination of a chimeric substrate, such as a chimeric Sic1 can be measured. A "chimeric substrate" is a substrate for an enzymatic reaction comprised of two or more heterologous polypeptides.

Thus, in one embodiment, the chimeric Sic1 is a maltose binding protein Sic1 chimera containing a myc epitopehexahistidine tag at the C-terminus (MBP-Sic1mycHis6). Following the contacting of the components of the reaction, aliquots of the ubiquitination assays are transferred from a first microtiter plate to a second microtiter plate with an appropriate surface. In one embodiment, reactions are transferred to a microtiter plate whose wells have been coated with a reagent that can capture the substrate (e.g., for MBP-Sic1p, wells coated with amylose, anti-MBP antibody, anti-myc antibody, anti-Sic1 p antibody, or NiNTA). After washing away unbound proteins, the substrate-coated wells can be directly imaged (e.g., for reactions performed with fluorescent or radio-labeled ubiquitin).

Alternatively, wells can be contacted with an appropriate reagent to capture derivatized ubiquitin (e.g., biotin-Ub, GST-Ub etc.) covalently linked to substrate MBP-Sic1mycHis6p. The wells would then be probed with reagents directed against the substrate (anti-MBP, anti-Sic1) to detect the extent of substrate-ubiquitin conjugates formed, or alternatively, a labeled substrate (fluorescent, radioactive) would be used and imaged directly. These assays are similar in design but yield distinct information, either of which can be used with the method of the invention. The first assay measures the total amount of ubiquitin incorporated into substrate, and the second measures the total fraction of substrate that becomes covalently linked to at least one ubiquitin molecule. Both of these assays can be used to differentiate between compounds that block the formation of the substrate-ubiquitin linkage versus those compounds that interfere with the elaboration of the substrate-linked polyubiquitin chains. All of the assays can be used to identify compounds that modulate the activities of an ubiquitin ligase.

Another assay for ubiquitination is a scintillation proximity assay. This assay uses beads containing a fluorescent substrate that emits light when activated by radioactive substances, and a means of conjugating the bead to ubiquitin. In one embodiment, the bead containing a fluorescent substrate is avidinated, and is contacted with biotinylated ubiquitin. A radiolabeled substrate, such as radiolabeled Sic1, is incubated with the beads in the presence of the reaction components. Ubiquitinated Sic1 is quantified by measuring bead fluorescence, which occurs only upon ubiquitination of the labeled Sic1. (See Bosworth, N. et al., *Nature* 341:167–168, 1989), incorporated herein by reference.)

A further embodiment of the invention provides a chimeric protein comprising a ubiquitin conjugating enzyme and conjugation substrate. Any of the ubiquitin conjugating enzymes and conjugation substrates disclosed above would be suitable for creating such a chimeric protein. A chimeric protein has the advantage of reducing the potential that substrate-targeting requirements will not be met in the performance of the assay method disclosed herein. Methods of producing chimeric proteins are well known in the art.

A still further embodiment of the invention provides methods of identifying polypeptides having ubiquitin ligase activity, or novel substrates. The test polypeptide, whether being tested for ubiquitin ligase activity or the ability to be ubiquitinated or conjugated, is incubated with known components of the assay system disclosed herein. Polypeptides having ubiquitin ligase activity will be easily identified by their ability to stimulate ubiquitination of a known substrate. Novel substrates are identifiable by the ability of known an ubiquitin ligase and ubiquitin conjugating enzyme to attach ubiquitin thereto.

In a further embodiment of the invention, there is provided a method of identifying an activity relationship between an ubiquitin ligase and an ubiquitin conjugating enzyme. By "activity relationship" it is meant that the activity of a particular ubiquitin ligase will stimulate the ubiquitination activity of a particular ubiquitin conjugating enzyme. It is unlikely that every ubiquitin ligase will stimulate the activity of every ubiquitin conjugating enzyme. Thus, a test ubiquitin ligase is contacted with a chimeric protein comprising a test ubiquitin conjugating enzyme and a conjugation substrate in the presence of an E1 enzyme, ubiquitin, and ATP, and autoubiquitination of the chimeric protein is measured. The presence of autoubiquitination indicates that the test ubiquitin ligase can stimulate the ubiquitin transfer activity of the test ubiquitin conjugating enzyme, thus the two proteins have an activity relationship. The identification of such an activity relationship allows for such enzymes to be paired in subsequent ubiquitination assay systems.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

In the examples described below the letter "h" indicates the human form of the gene or protein and the letter "y" designates the yeast (e.g., *Saccharomyces cerevisiae*) form of the gene or protein. For example "hCdc4" indicates the human Cdc4 gene and "yCdc34p" indicates the yeast Cdc34 polypeptide.

MATERIALS AND METHODS

Yeast strains and reagents. Yeast strains, plasmids, and a HeLa cDNA library for the two-hybrid screen were a generous gift from R. Brent (Massachusetts General Hospital, Boston, Mass.). Wx131.2c cdc53-2$^{ts}$ strain was obtained from M. Goebl (Indiana University, Indianapolis, Ind.). Baculoviruses expressing hCDK2$^{HA}$, hCyclin A (D. Morgan, UCSF, San Francisco, Calif.), SKP2 (H. Zhang, Yale, New Haven, Conn.), hSkp1 (P. Sorger, MIT, Cambridge, Mass.) and plasmids pGEX-KG-hSkp1, pGEX-KG-SKP2 (P. Jackson, Stanford, Palo Alto, Calif.), pCS2+ nµgal, pCS2+HA-SMC1 (S. Handeli, FHCRC, Seattle, Wash.) were kindly provided by the indicated investigators. Other baculoviruses were previously described (Feldman, R. M. R., et al. *Cell* 91:221–230, 1997). Ubiquitin and the Protein Biotinylation Kit were purchased from Sigma, and biotinylated ubiquitin was prepared according to the manufacturer's instructions. Ubiquitin aldehyde was a generous gift from R. Cohen (University of Iowa, Iowa City, Iowa).

Plasmid and baculovirus construction. Full length hCul1 ORF was assembled from ESTs HE2AB96 and HSVAD74 and subcloned into pRS316 and pMALc (New England Biolabs). The same hCul1 fragment was also subcloned into pVL1393 (PharMingen) to generate an hCul1-expressing baculovirus. An N-terminal epitope-tagged version of hCul1 was constructed by inserting a DNA cassette that contains two tandem repeats of the Polyoma epitope (MEYMPME) followed by six histidine residues (designated as PHis6) into pRS316-hCul1. $^{PHis6}$hCul1 fragment was then subcloned into pFASTBAC1 (Gibco BRL) to generate a $^{PHis6}$hCul1 baculovirus, and pDNA3.1/Zeo (Invitrogen) to generate pcDNA3.1-PHis6-hCul1. pCS2+HA-hSkp1 was generated by subcloning a hSkp1 fragment from pGEX-KG-hSkp1 into pCS2+HA-SMC1.

Antibodies. Anti-hCul1 antibodies were generated in rabbits immunized with either a fusion protein containing the first 41 residues of hCul1 followed by GST (BAbCO), or a fusion protein containing GST followed by the last 86 residues of hCul1 (Caltech antibody facility). Antibodies against hCul1 and GST were affinity purified using MBP fusions of the corresponding peptides and GST, respectively, as described (Harlow, E., and Lane, D., *Antibodies: A Laboratory Manual,* Cold Spring Harbor Laboratory, Cold Spring Harbor, N.Y., 1988). Monoclonal anti-Polyoma antibodies were bound to protein A-Sepharose beads and cross-linked to protein A with dimethylpimilimadate (Harlow and Lane, 1988, supra) at a concentration of approximately 2 mg of antibodies per ml of protein A resin. Anti-HA resin was generated by coupling 1 ml of anti-HA ascites to 1 ml of CNBr activated agarose (Pharmacia Biotech) according to the manufacturer's protocol.

Expression and purification of proteins. Proteins expressed in bacteria or yeast were purified according to standard protocols and as described (Feldman, R. M. R., *Cell* 91:221–230, 1997). For the expression and purification of chimeric SCF complexes, Hi5 insect cells were infected with baculoviruses expressing $^{PHA}$Cdc4 (PHA designates an epitope-tag consisting of two tandem repeats of the Polyoma epitope followed by three hemagglutinin epitopes), $^{Cdc53pHA}$, $^{PHis6}$hCul1 (MOIs of 6), ySkp1$^{His6}$, or hSkp1 (MOIs of 4). Seventy-two hours postinfection, cells were collected and lysates were prepared as described (Feldman et al., 1997, supra). The Polyoma tagged proteins were affinity-purified from these lysates (Feldman et al., 1997, supra) to yield the various SCF complexes.

Cell cultures and transfections. WI-38 human lung fibroblasts were purchased from ATCC. HeLa S3 cells were a gift from S. Handeli (FHCRC, Seattle, Wash.). Cells were grown in DMEM-F12 (Gibco BRL) supplemented with 10% FBS (Gibco BRL) at 37° C./5%CO$_2$. Cells were transfected in 100 mm dishes by the modified calcium phosphate method (Chen, C., and Okayama, H., *Mol. Cell. Biol.* 7:2745–2752, 1987). 10 μg pCS2+HA-hSkp1 and 7.5 μg pcDNA3.1-PHis6-hCul1 vectors were used per transfection plate. Transfection efficiency was monitored by cotransfection of 2.5 μg pCS2+nμgal plasmid per transfection plate followed by standard colorimetric gal assays (Sambrook, J., et al., *Molecular cloning: Assay for μ-galactosidase in extracts of mammalian cells,* Cold Spring Harbor Laboratory Press, Cold Spring Harbor, N.Y., 1989). Total DNA concentration was 20 μug/100 mm dish and was adjusted for every transfection plate by adding empty vectors. Cells were harvested and lysed 24 hr posttransfection.

Immunoprecipitations and Western blotting. Baculovirus-infected insect cells were harvested and lysed at 48 hr (for Sf9 cells) or 72 hr (for Hi5 cells) postinfection in 0.8 ml of lysis buffer per 100 mm plate (as described in Feldman, R. M. R., et al. *Cell* 91:221–230, 1997). Metabolic labeling was done by incubating insect cells for 3 hr in methionine-deficient medium plus 20 μCi/ml of Tran[$^{35}$S]-label prior to lysis. WI-38 and HeLa S3 cells were lysed in 0.4 ml of lysis buffer per 100 mm plate. Lysates were cleared by centrifugation at 14,000 g for 15 min, adjusted to 10% glycerol, frozen in liquid nitrogen, and stored at −80° C. Cell lysates (1 mg) were incubated with 50 μl of antibody-coupled beads (1:1 suspension in lysis buffer) for 2 hr at 4° C. Precipitates were washed five times with 1 ml of lysis buffer and analyzed by SDS-PAGE followed by Western blotting or autoradiography. Western blotting was performed as described (Harlow, E., & Lane, D., *Antibodies: A Laboratory Manual,* Cold Spring Harbor Laboratory, Cold Spring Harbor, N.Y., 1988). $^{PHis6}$hCul1 and $^{HA}$hSkp1 were detected by rabbit polyclonal anti-hCul1 and biotinylated anti-HA (12CA5) primary antibodies and visualized by incubation with goat anti-rabbit-HRP and streptavidin-HRP conjugates, followed by ECL detection (Amersham).

Ubiquitination reactions. Crude Sf9 cell lysates (500 μg) prepared from cells infected with $^{Phis6}$hCul1 baculovirus were incubated with 20 μl anti-Polyoma beads for 2 hr at 4° C. to allow $^{Phis6}$hCul1 binding. Beads were washed three times with lysis buffer and incubated with 1 mg of crude HeLa S3 lysate overnight at 4° C. Beads were then washed three times with lysis buffer and supplemented with 6 μg biotinylated ubiquitin (BUb), 500 ng hCdc34, 25 ng $^{His6}$yUBA1, 1 μl of 10×ATP-regenerating system (Feldman, R. M. R., et al., *Cell* 91:221–230, 1997), 1 μl of 10×reaction buffer (Feldman et al., 1997, supra), and 0.5 M ubiquitin aldehyde. Reactions were adjusted to 10 μl by adding 20 mM HEPES [pH 7.6], 100 mM KOAc, 1 mM DTT, incubated for 90 min at 30° C., and terminated by adding Laemmli sample buffer. Samples were analyzed by Western blotting with streptavidin-HRP conjugate. All ubiquitination reactions with chimeric SCF complexes were performed as described (Feldman et al., 1997, supra).

Although the invention has been described with reference to the presently preferred embodiment, it should be understood that various modifications can be made without departing from the spirit of the invention. Accordingly, the invention is limited only by the following claims.

What is claimed is:

1. A method of identifying a compound that modulates an activity of a ubiquitin ligase, comprising:

(a) contacting a test compound under suitable ubiquitination conditions with a mixture comprising ubiquitin, a ubiquitin-activating E1 enzyme, adenosine triphosphate (ATP), yeast ubiquitin-conjugating enzyme Cdc34, a substrate comprising a chimeric protein comprising a ubiquitin conjugating enzyme and a conjugation substrate, 1 and an ubiquitin ligase selected from the group consisting of yeast ubiquitin ligase Cdc53, and Cdc53-related human cullins Cul1, Cul2, Cul3, Cul4, Cul5 and Cul6;

(b) measuring the ubiquitination of said substrate under the conditions of (a); and (c) comparing the ubiquitination of said substrate as measured in (b) to ubiquitination of said substrate in the mixture when not contacted with said test compound to determine a difference in the ubiquitation of said substrate, wherein the difference is indicative of the ability of said test compound to modulate ubiquitin ligase activity.

2. The method of claim 1, wherein ubiquitin ligase activity is stimulated.

3. The method of claim 1, wherein ubiquitin ligase activity is inhibited.

4. The method of claim 1, wherein said compound is an antibody, a non-antibody polypeptide, a carbohydrate, a lipid, or a chemical compound.

5. The method of claim 4, wherein said antibody is a monoclonal antibody.

6. The method of claim 1, wherein said ubiquitin ligase is mammalian.

7. The method of claim 6, wherein said ubiquitin ligase is human.

8. The method of claim 1, wherein said ubiquitin ligase is selected from the group consisting of Cdc53-related human cullins Cul1, Cul2, Cul3, Cul4, Cul5 and Cul6.

9. The method of claim 1, wherein said substrate is the ubiquitin conjugating enzyme.

10. The method of claim 1, wherein said conjugation substrate is selected from the group consisting of cyclin-dependent protein kinase inhibitor Sic1, p53, cyclin D1, cyclin E, cyclin A/CDK2, and G1 cyclin.

11. The method of claim 1, wherein said ubiquitin is a derivatized ubiquitin selected from the group consisting of a $^{125}$I-ubiquitin, a flourescent ubiquitin, glutathione-S-transferase ubiquitin, and a biotinylated ubiquitin.

12. The method of claim 1, wherein said compound is a chemical compound.

13. A method of identifying a polypeptide having ubiquitin ligase activity, comprising:

incubating a test polypeptide with an E1 enzyme, ubiquitin, ATP, and a substrate comprising a chimeric protein comprising a ubiquitin conjugating enzyme and a conjugating substrate, under suitable ubiquitination conditions and measuring the ability of said test polypeptide to attach ubiquitin to said substrate.

14. The method of claim 13, wherein said test polypeptide is a mammalian polypeptide.

15. The method of claim 14, wherein said test polypeptide is a human polypeptide.

* * * * *